(12) United States Patent
Burkart et al.

(10) Patent No.: US 8,689,625 B2
(45) Date of Patent: Apr. 8, 2014

(54) METHOD AND APPARATUS FOR DETECTING THE LEVEL OF A LIQUID IN MONITORING A DISPENSE/ASPIRATE PROCESS

(75) Inventors: Michael Burkart, Waldbronn (DE); Martin Trump, Pforzheim (DE)

(73) Assignee: Stratec Biomedical AG (DE)

( * ) Notice: Subject to any disclaimer, the term of this patent is extended or adjusted under 35 U.S.C. 154(b) by 339 days.

(21) Appl. No.: 13/278,364

(22) Filed: Oct. 21, 2011

(65) Prior Publication Data

US 2012/0096940 A1    Apr. 26, 2012

(30) Foreign Application Priority Data

Oct. 21, 2010   (DE) .......................... 10 2010 049 037

(51) Int. Cl.
*G01F 23/00* (2006.01)
*B01L 3/02* (2006.01)
*G01N 25/20* (2006.01)

(52) U.S. Cl.
USPC .............................. 73/295; 422/552; 436/147

(58) Field of Classification Search
USPC ........... 73/295; 436/147; 422/82.12, 551–553
See application file for complete search history.

(56) References Cited

U.S. PATENT DOCUMENTS

| | | | |
|---|---|---|---|
| 5,078,164 A | 1/1992 | Doellgast | |
| 5,186,760 A | 2/1993 | Rubenzer | |
| 6,602,714 B1 * | 8/2003 | Tagge et al. | 506/37 |
| 7,033,840 B1 * | 4/2006 | Tagge et al. | 436/147 |
| 7,049,558 B2 * | 5/2006 | Baer et al. | 219/548 |
| 7,607,823 B2 | 10/2009 | Kent | |
| 7,981,362 B2 * | 7/2011 | Glezer et al. | 422/50 |
| 2002/0144994 A1 | 10/2002 | Golan | |
| 2004/0241869 A1 * | 12/2004 | Davies et al. | 436/147 |
| 2005/0028587 A1 * | 2/2005 | Baer et al. | 73/204.26 |
| 2005/0142033 A1 * | 6/2005 | Glezer et al. | 422/58 |
| 2006/0133448 A1 | 6/2006 | Kearney | |

FOREIGN PATENT DOCUMENTS

| | | |
|---|---|---|
| DE | 4118952 A1 | 12/1991 |
| DE | 19944331 B4 | 3/2006 |
| EP | 1605245 A2 | 12/2005 |
| EP | 1637887 A1 | 3/2006 |
| JP | 5717060 A | 9/1982 |
| JP | 03028721 A | 2/1991 |
| WO | 8701616 A1 | 3/1987 |
| WO | 9116979 A2 | 11/1991 |

\* cited by examiner

*Primary Examiner* — Hezron E Williams
*Assistant Examiner* — Nathaniel Kolb
(74) *Attorney, Agent, or Firm* — Cantor Colburn LLP

(57) ABSTRACT

A device and a method are used for measuring the filling level of a fluid for monitoring a dispense/aspirate process in reaction vessels, including at least one cavity for dispensing and aspirating the fluid, where the cavity is provided with a filling level sensor whose signals, transmitted to an evaluation unit, are evaluated to determine the filling level, the at least one cavity is assigned a receiving body which is closed at the bottom and is separated from the cavity for receiving the fluid, the filling level sensor is at least one thermistor extending along the outside of a wall of the receiving body without coming in contact with the fluid, the evaluation unit evaluates the temperature influence of the thermistor in dispensing, aspirating and in retention of the fluid in the receiving body to detect the filling level, in this way the process monitoring in washing the reaction vessels is improved.

10 Claims, 4 Drawing Sheets

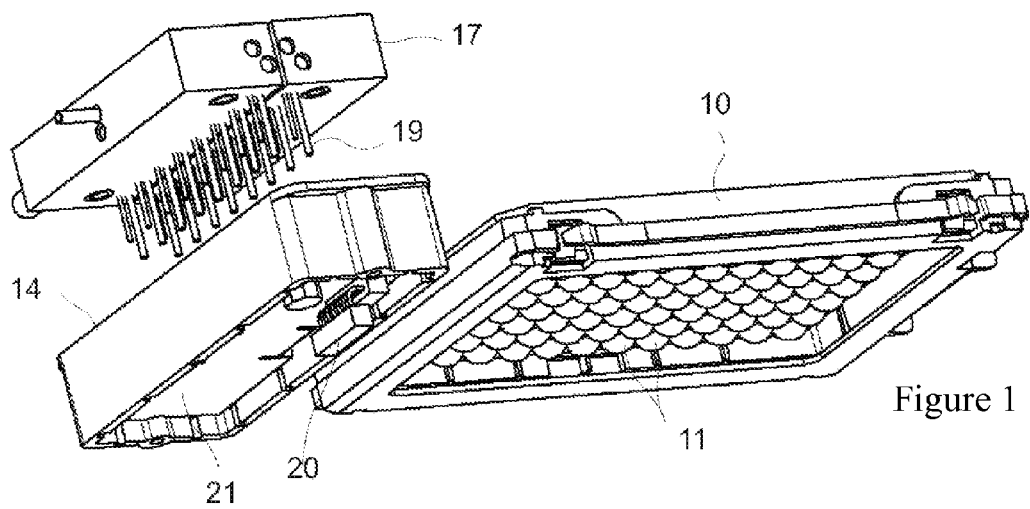
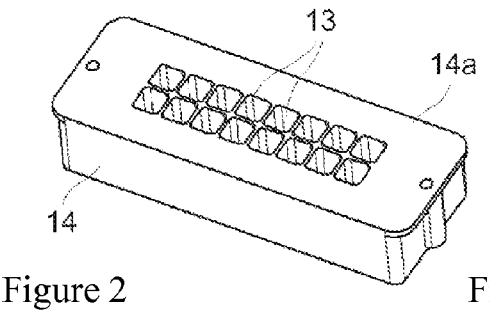
Figure 2
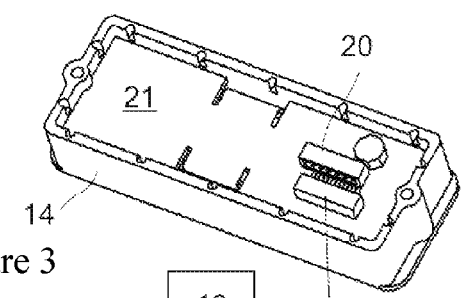
Figure 3

METHOD AND APPARATUS FOR DETECTING THE LEVEL OF A LIQUID IN MONITORING A DISPENSE/ASPIRATE PROCESS

TECHNICAL FIELD

The invention relates to a device for detecting the filling level of a fluid for monitoring a dispense/aspirate process in reaction vessels by means of a filling level sensor and a corresponding method.

BRIEF DESCRIPTION OF RELATED ART

As part of medical technical equipment, reaction vessels such as microtiter plates are used as laboratory equipment for investigating properties. Most rectangular microtiter plates are made of plastic, or for special applications they may also be made of glass. They have numerous mutually isolated cavities, also known as wells, arranged in rows and columns. These microtiter plates must be washed regularly. Such a washing apparatus is known from EP 1 605 245 A2, for example, where temperature sensors and filling level sensors are used, but the main attention is on the multistage washing operation. Fluid is usually dispensed to the microtiter plate in a microplate washer and then aspirated out later. Microtiter plates usually have a plurality of wells (for example, wells in a number of 6, 12, 24, 96, 384 or 1536 are customary), so the washing is performed by using a washing head which distributes the fluid among multiple wells at the same time, for example. The flow of fluid through the washing head and its distribution to two rows of eight (sixteen channels), for example, is not monitored. Monitoring whether and how much fluid has flowed through each of the sixteen channels and whether it has been aspirated can therefore be done only indirectly.

In the past, the following methods have been used for washing such reaction vessels:

Optical methods in which a previously dispensed quantity of fluid is aspirated and the flowing column of fluid in a channel is observed by means of photoelectric bearers or similar sensors. By evaluating the air-fluid boundaries over time, it is possible to determine indirectly the quantity of fluid dispensed and aspirated. However, this method depends greatly on the properties of the fluid as well as many other influencing parameters (flow rate, foaming, condition of the channel, etc.). A reliable determination of the fluid volume is possible only to a limited extent. Furthermore, optical methods depend on the varying transparency of the various media to be measured.

The conductivity method with electrically conductive fluids. Two electrically conductive contacts are situated in a container, preferably on the bottom and at a defined height (e.g., DE 199 44 331 B4). The fluid added to the container short-circuits the contacts, thus also allowing the volume to be determined. One problem with this method may be the formation of foam or the development of a conductive crystal bridge which fills up over time and can occur when the fluid to be measured dries up. There may thus be faulty detection due to electrical bridging. A reliable determination of the fluid volume is possible only to a limited extent. Likewise there may be metallic components in the fluid which may cause contamination. This is then followed by a complex and frequent cleaning of the measurement container.

A certain quantity of fluid is dispensed individually to each channel and then aspirated as needed. In this case, the fluid is not distributed to eight dispensing channels, for example, by means of only one pump, as is customary, but instead each channel is serviced by its own "pump." For example, 8-channel hose pumps may be used here. With regard to costs, tubing complexity and flexibility, however, this method has major disadvantages.

JP 57147060 A describes a device for chemical analysis in which a thermistor on the outside of a pipette may be used to detect a solid-gaseous and/or gaseous-solid change of state of the medium at a certain location in the pipette. A filling level measurement level along a certain area is then impossible. Furthermore, the thermistor may come in contact with the fluid on immersion of the pipette in the fluid and may thus become contaminated.

JP 03028721 A has a thermistor which is provided for determination of a certain fluid level and/or passage of a media boundary; this thermistor is covered by a cover glass which comes in contact with the fluid. The glass and therefore the thermistor embedded in it or covered by it then become contaminated by the fluid.

EP 1 637 887 A1 describes a device for rinsing titer plates, in which lines are cleaned by ultrasound. Proposals for detecting the filling level can be found in paragraph [0014] to the extent that detection may be performed by means of capacitive measurement, with ultrasound, optically or by direct contact measurement.

U.S. Pat. No. 7,607,823 B2 describes the use of thermistors for detection of leakage. The thermistor is in contact with the fluid, which can result in contamination of the thermistor.

DE 10 2004 026 396 B4 describes a resistance arrangement for measuring the filling level in a fluid, wherein the resistance arrangement is immersed in the fluid. This may lead to contamination of the arrangement. Within the scope of this principle, several resistance segments connected in series are used.

US 2006/0133448 A1 discloses a comparable arrangement, but the thermistor sensor there, which is encased in a cover, is surrounded by fluid, for which purpose corresponding openings are provided in the cover. Contamination is still possible.

DE 41 18 952 C2 discloses a filling level sensor in which the heating element and the sensor are separate from one another but are connected in a thermally conducting manner. There is no reference to laboratory automation in this patent.

Washing systems for microtiter plates are also described in U.S. Pat. No. 5,186,760 A, U.S. Pat. No. 5,078,164 A, WO 91/16979 A2 and WO 87/01616 but no devices for measuring the filling level are described at all or they are not described in detail.

The use of a thermistor per se to determine the composition of a fluid is known from US 2002/0144994 A1, for example.

BRIEF SUMMARY

Against the background of this prior art, the invention improves upon the process monitoring in washing reaction vessels.

At least one cavity of the reaction vessel, e.g., a microtiter plate, is paired with a receiving body which is closed at the bottom and is separated from the cavity, at least one thermistor being provided on the walls of the receiving body on the outside, i.e., without any contact with the fluid, to serve as the filling level sensor. This thermistor is preferably embodied as a temperature-dependent PTC resistor. By applying the power supply voltage, the thermistor is kept in a working range in which the inherent heating by means of the electric current established and the associated increase in resistance are in equilibrium. When filling the receiving body, which is kept separate from the reaction vessel and is or can be assigned to the cavity, there is a transfer of heat from the fluid to the thermistor, so that the thermistor is cooled. This cooling leads to a change in resistance which leads to a detectable change in voltage. This change in voltage is used as a signal and/or as a measured variable and indicator for the filling level and also for the volume if the container geometry is known. The dispense and/or aspirate procedure or the retention of a fluid can thus be detected and the process can be monitored.

Due to the arrangement of the thermistor on the outside of the wall of the receiving body, the wall is heated due to the self-heating of the thermistor and nevertheless there is a good thermal binding to the fluid with a thin wall thickness accordingly. The most direct possible and nevertheless indirect temperature transition improves the response of the filling level sensors but on the other hand it also ensures that noncontact detection of the fluid is possible without any risk of contamination.

Since the monitoring of the sixteen channels and/or cavities, for example, is usually performed only indirectly when washing microtiter plates, the dispensing of fluids is performed by using an additional receiving container which has, for example, the same number (e.g., sixteen) of receiving bodies as channels. This trough having sixteen cavities, for example, may be constructed so that each cavity is assigned a corresponding thermistor so that each channel can be monitored separately with regard to its filling level.

Each thermistor is preferably part of a measurement bridge with which measurements are performed based on a reference thermistor. This reference thermistor has the same resting temperature as the thermistor used for the measurement but it is not affected by the filling level. Therefore the voltage offset of the measurement circuit which is otherwise present is eliminated on the one hand while on the other hand the influence of ambient temperature and other factors can also be minimized at the same time.

In addition to determining the filling level, a volume verification is also to be achieved in a certain accuracy range if the geometry is known, especially since the thermistor is usually operated in the steep range of its characteristic line.

Additional advantages are derived from the subclaims and the following description of one exemplary embodiment.

BRIEF DESCRIPTION OF THE FIGURES

The invention is described in greater detail below on the basis of an exemplary embodiment depicted in the accompanying figures, in which:

FIG. 1 shows a reaction vessel in the form of a microtiter plate with the respective washing head and receiving container, FIG. 2 shows the receiving container with the respective receiving bodies in a view from above, FIG. 3 shows a view of the receiving container from below with a view of the sensor circuit board.

DETAILED DESCRIPTION

Figure 4:
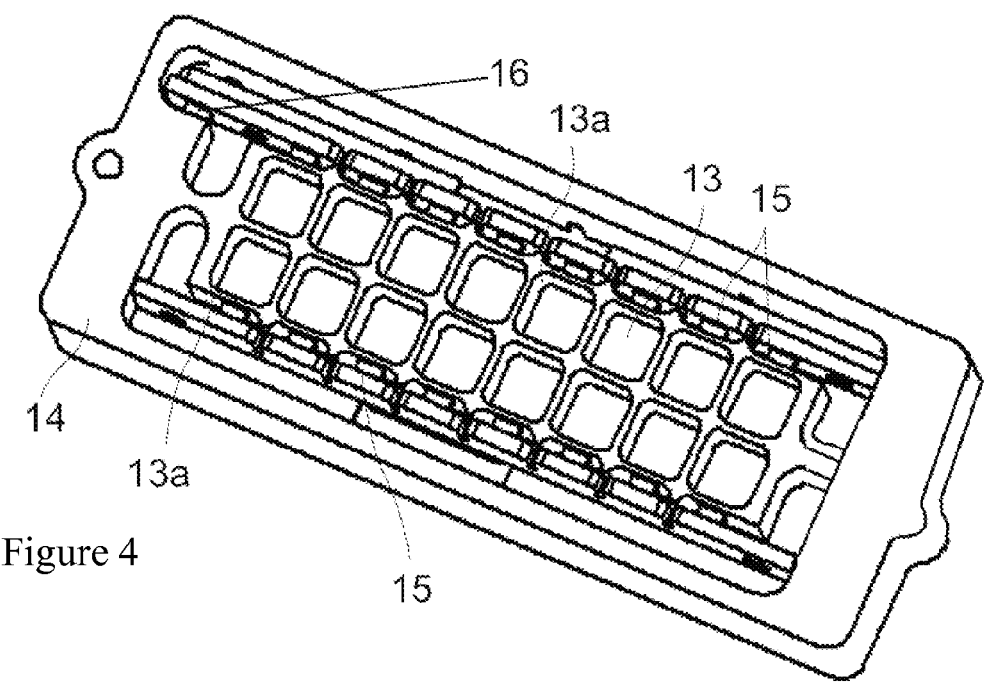
FIG. 4 shows a view of the receiving container from FIG. 2 as seen from above with the cover removed, showing the sensor system.

Before the invention is described in detail, it should be pointed out that it is not limited to the respective components of the device or the respective process steps because these components and methods may vary. The terms used here are intended only to describe particular embodiments and are not used in a restrictive sense. Furthermore, if the number one or an indefinite article is used in the description or in the claims, this should also be understood to include a plurality of these elements as long as the overall context does not clearly indicate something to the contrary.

FIGS. 1 through 4 show a device for detecting the filling level of a fluid and/or the volume of a fluid in a reaction vessel such as a microtiter plate 10 having a plurality of cavities, so-called wells 11 for dispensing and aspirating a fluid. When the invention is explained below on the basis of a microtiter plate, the device and the method shown here and described in detail for detecting the filling level of a fluid may also be used in very general terms for monitoring a dispense/aspirate process in reaction vessels, in particular in the laboratory area.

FIG. 1 shows, in addition to the microtiter plate, a washing head 17 with pipettes 19, which are arranged above a receiving container 14, a view of which can be seen in FIG. 2. The fluid is dispensed into the well through the pipettes and is aspirated out of them. The trough-shaped receiving container 14 has a plurality of receiving bodies 13 in its cover 14a, these receiving bodies being closed at the bottom and arranged in two rows of eight corresponding to sixteen receiving bodies in the exemplary embodiment. A sensor circuit board 21 having an interface 20 is arranged on the bottom side, the interface being connected to the evaluation unit 12 which is diagramed schematically in FIG. 3.

Such microtiter plates 10—as well as other reaction vessels—are used as laboratory equipment for testing biological properties, for example, for measuring absorption in photometers in pharmaceutical and plant protection research, for example, or also in the medical technical field. These microtiter plates are usually rectangular and made of plastic, but they may also be made of glass. They contain many mutually isolated cavities known as wells arranged in rows and columns. The usual number of wells varies in the range of 6, 12, 24, 96, 384 or 1536 wells. For cleaning the microtiter plates, a microplate washer dispenses fluid into the microtiter plate and then later aspirates it again. In the exemplary embodiment in FIG. 1, the microtiter plate has 96 wells, divided into twelve rows of eight. The washing head 17 distributes fluid between two rows of eight corresponding to sixteen channels at the same time. The flow of fluid through the washing head and its distribution among the sixteen channels is not monitored. Monitoring whether and how much fluid has flowed through each of the sixteen channels and whether this has been aspirated can therefore be performed only indirectly.

According to the invention, at least one cavity is provided in the reaction vessel, and a receiving body 13 with a filling level sensor is or may be assigned to the at least one cavity. The filling level sensor is formed by at least one thermistor 15 extending along the outside over an area that is required for the determination of the filling level, and the thermistor is arranged on the outside along the wall 13a of the receiving body 13. Essentially it is possible to assign more than one thermistor to the wall 13a. Likewise, usually not just one of the receiving bodies 13, which can be assigned to a cavity, is equipped with a filling level sensor, but all receiving bodies are equipped with a filling level sensor. The evaluation unit 12 determines the influence of temperature of the thermistor 15 in dispensing, aspirating and in retention of the fluid for a determination of the filling level and/or if the geometry of the receiving body is known, for a determination of the volume.

In the exemplary embodiment, the filling level measurement is performed on the receiving container 14 which is kept separate from and at a distance from the microtiter plate 10 and has the receiving bodies 13 which is or may be assigned to the cavity for receiving the fluid. The thermistor 15 is arranged on the outside of the wall 13a without contact with the liquid to avoid any contamination according to FIG. 4.

By dispensing the fluid into the additional trough-shaped receiving container 14 having n receiving bodies 13 which correspond to the sixteen channels of the washing head in each channel individually, each channel can be observed individually. The filling level and thus also the quantity of fluid in the receiving container 14 having n receiving bodies 13 can be ascertained by the thermistor 15 based on the temperature-dependent PTC resistances of the thermistors. The receiving body 13 preferably has a low mass and the wall thicknesses of the wall 13a are low accordingly. Since the filling level sensors in the form of the thermistors 15 are situated on this wall, a small wall thickness leads to a good thermal binding of the sensor system. This temperature transition is as direct as possible, improving the response performance of the sensors when there is a change in the filling level of the fluid.

Figure 5:
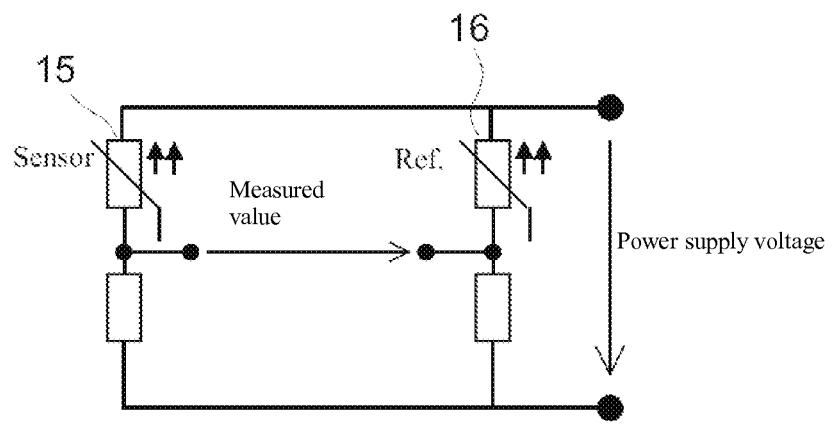
FIG. 5 shows a circuit diagram of the measurement bridge.

The resistance of the thermistor is part of a measurement bridge according to FIG. 5 in which a measurement is performed based on a reference thermistor 16 according to FIG. 4. The reference thermistor 16 measures the temperature of the receiving container 14, which may also be utilized for temperature compensation with respect to the environment and its influences. The reference thermistor 16 has the same resting temperature as the at least one thermistor 15 used for the measurement but it is not affected by the filling level. Therefore the voltage offset of the measurement circuit which is otherwise present is eliminated while at the same time the influence of the ambient temperature and other factors are minimized.

Figure 6:
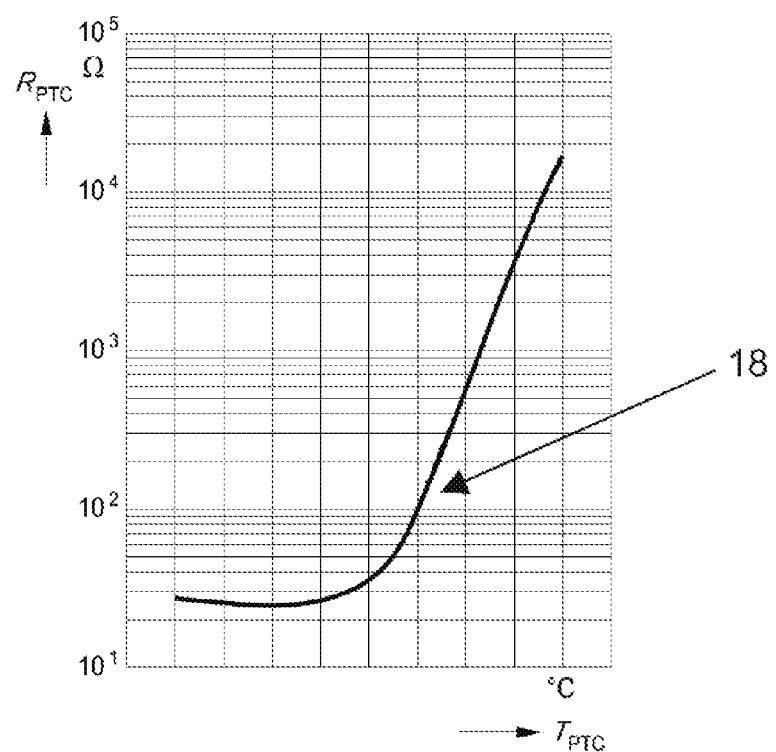
FIG. 6 shows a characteristic line of a thermistor in which the resistance is plotted as a function of the temperature.

By applying the power supply voltage, the thermistor 15 heats up to a specific temperature which corresponds to the operating point 18 according to FIG. 6. At this operating point, the inherent heating due to the electric current established and the associated increase in resistance are in equilibrium.

The thermistor heats up due to the heating and it also heats up the wall when it is in contact with the wall 13a in this area. When the container is filled, there is a transfer of heat from the heated wall to the fluid so that the thermistor 15 is also cooled. Since the thermistor is operated in a very steep range of its characteristic line in FIG. 6, even minor changes in temperature result in a relatively great change in resistance. If the value of the thermistor changes, the conditions in the measurement bridge are shifted, so that a change in voltage, which is proportional to the change in resistance, can be measured. This change in voltage is used as a measured variable and indicator of the filling level and/or if the container geometry is known, as an indicator of the volume.

In the exemplary embodiment, there is a plurality of receiving bodies 13 in the receiving container 14, such that at least one thermistor 15 is assigned to each receiving body 13 according to FIG. 4. The number of receiving bodies 13 is thus fewer than or equal to the number of wells 11 in the microtiter plate 10. In the exemplary embodiment, sixteen receiving bodies must be compared with 96 wells. The thermistor 15 preferably has a positive temperature coefficient, but essentially it could also have a negative temperature coefficient. It is likewise conceivable to use separate heating resistors and separately positioned temperature sensors instead of the thermistors, but this would be a more complex approach.

Although known methods have problems due to foam and crystal deposits and the bridge formations associated therewith or must rely on the transparency of the media, e.g., in optical methods, or they may also have to be decontaminated rapidly, the inventive approach does not have to combat these difficulties. The sensor system and the peripheral electronic system do not come in direct contact with the fluid. Physically and chemically, they are completely separate. This measurement method can be implemented structurally in tight spaces. Cross talk between the closely placed cavities can be minimized in the measurement. By reference measurements, the ambient conditions, e.g., the ambient temperature can be minimized as an influencing factor on the measurement. The measurement method allows automated verification of the dispensing behavior as well as the aspiration behavior of a microplate washer without any external intervention. This automated process is very important in suitably complex diagnostic systems. The process control is also greatly improved in this way.

Figure 7:
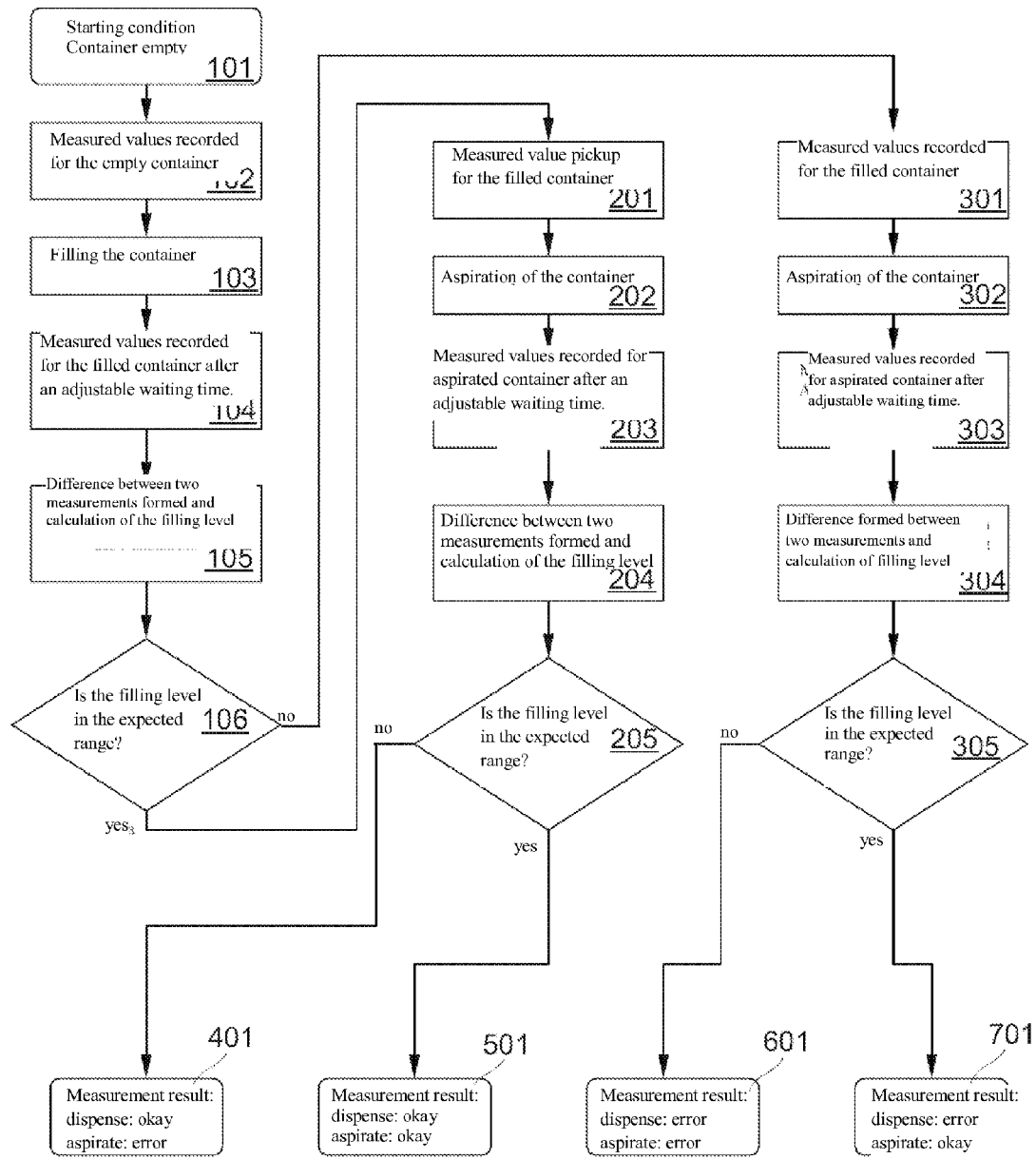
FIG. 7 shows a flow chart of the measurement.

According to the process, two measurements are performed to monitor the filling level according to FIG. 7. The first measurement is performed after filling the container while the second is performed after aspiration of the fluid from the receiving body 13. According to FIG. 7, the following steps are performed in doing so:

In the starting state according to step 101, the receiving container 14 and/or its receiving bodies 13 are empty. Then according to step 102, measured values are recorded for the empty container. Next the container is filled in step 103. Then a measured value for the filled container is recorded after an adjustable waiting time in step 104. The difference between the two measurements leads to the calculation of the filling level according to step 105, namely in filling the receiving body and/or container.

In step 106 there is an inquiry as to whether the filling level ascertained is in the expected range. If the filling level in step 106 is within the expected range, then according to step 201 a measured value is recorded for the filled container and in step 202 the fluid is aspirated from the container and in step 203 a measured value is recorded for the aspirated container again after an adjustable waiting period. The difference between the two measurements is determined, leading to calculation of the filling level in step 204, namely after the aspiration, and then the next inquiry is made in step 205. With steps 101 to 105, the first measurement is performed, while the second measurement is performed with steps 201 to 204. If the filling level is within the expected range in step 205, then according to step 501, the measurement results are in the expected range in filling as well as in aspiration or in dispensing and aspiration, i.e., the measurement results are in order. If the result is not within the expected range at the second measurement in step 205, i.e., in aspiration, then the dispensing was in order but the aspiration was not functioning properly, which would lead to the measurement result in step 401.

If the filling operation in step 106 is not within the expected range, then the measurements are performed according to step 301 to 304 which are analogous to the steps 201 to 204 to this extent. In step 305 the suction operation is queried, i.e., whether the filling level is within the expected range. If the answer there is yes, then the result according to step 701 is obtained from the combination of results from steps 106 and 305, i.e., the dispensing was defective but the aspiration was in order. If the filling level was not in the expected range after aspiration in step 305, then the measurement result in step 601 reveals that both the dispensing and the aspiration were defective.

Essentially the filling level can be determined not only during filling and aspiration but also while a fluid remains in the cavity.

The invention claimed is:

1. A device for detecting a filling level of a fluid for monitoring a dispense/aspirate process in reaction vessels comprising
    at least one cavity for dispensing and aspirating the fluid,
    at least one filling level sensor assigned to at least one cavity,
    an evaluation unit for evaluating signals transmitted by the at least one filling level sensor to determine the filling level,
    wherein a receiving body for receiving the fluid, the receiving body being closed at its bottom and separated from the at least one cavity, is assigned to at least one cavity,
    wherein the filling level sensor is at least one thermistor which extends along an outside of a wall of the receiving body without coming in contact with the fluid and
    wherein the evaluation unit evaluates a temperature influence of the thermistor in dispensing, aspirating or in retention of the fluid in the receiving body to detect the filling level.

2. The device according to claim 1, wherein a plurality of cavities and a plurality of receiving bodies are provided in a receiving container such that at least one thermistor is provided on the outside of the wall of each receiving body.

3. The device according to claim 2, wherein the plurality of receiving bodies in the receiving container is less than or equal to the plurality of cavities in the reaction vessel.

4. The device according to claim 1, wherein the at least one thermistor is a measurement bridge having a reference thermistor which is not influenced by the filling level of the fluid.

5. The device according to claim 1, wherein the thermistor has a positive temperature coefficient or a negative temperature coefficient.

6. The device according to claim 1, wherein the reaction vessel is a microtiter plate.

7. A method for detecting a filling level of a fluid for monitoring a dispense/aspirate process in reaction vessels having at least one cavity, comprising the steps
    assigning a filling level sensor to the at least one cavity,
    evaluating signals transmitted by the filling level sensor to determine the filling level,
    arranging at least one thermistor as the filling level sensor without coming in contact with the fluid along a outside of a wall of a receiving body which is separated from the at least one cavity and can be allocated to the at least one cavity, the receiving body being provided for receiving the fluid, which is intended for the at least one cavity, and being closed at its bottom,
    detecting an influence of temperature or a change in resistance of the thermistor in dispensing, aspirating or retention of the fluid in the receiving body to determine the signals,
    evaluating the signals detected by the thermistor and transmitted to an evaluation unit for determining the filling level.

8. The method according to claim 7, wherein the signals detected by the thermistor are equalized within a measurement bridge with a reference thermistor which is not influenced by the filling level of the fluid.

9. The method according to claim 7, wherein a measurement of the filling level is performed in two steps, including dispensing and aspirating the fluid in multiple receiving bodies simultaneously with evaluation of results of individual receiving bodies.

10. The method according to claim 7, wherein a microtiter plate is used as the reaction vessel.

* * * * *